United States Patent [19]

Nuss

[11] Patent Number: 5,789,750
[45] Date of Patent: Aug. 4, 1998

[54] OPTICAL SYSTEM EMPLOYING TERAHERTZ RADIATION

[75] Inventor: Martin C. Nuss, Fair Haven, N.J.

[73] Assignee: Lucent Technologies Inc., Murray Hill, N.J.

[21] Appl. No.: 711,146

[22] Filed: Sep. 9, 1996

[51] Int. Cl.$^6$ .......................... G01N 21/17; G01N 21/49
[52] U.S. Cl. ................... 250/338.1; 250/330; 250/341.1
[58] Field of Search .............................. 250/338.1, 330, 250/341.1

[56] References Cited

U.S. PATENT DOCUMENTS 5,623,145  4/1997  Nuss ........................................ 250/330

OTHER PUBLICATIONS

R. Takahashi et al, "Ultrafast 1.55μm photoresponses in low–temperature–grown InGaAs/InAlAs quantum wells", *Appl. Phys. Lett. 65 (14)*, 3 Oct. 1994, pp. 1790–1792.
M. C. Nuss, "Chemistry is Right for T–Ray Imaging", 1996 IEEE Pamphlet No. 8755–3996/96, Mar. 1996, pp. 25–30.
R. A. Cheville, et al., "Time domain terahertz impulse ranging studies", *Appl. Phys. Lett 67 (14)*, 2 Oct. 1995, pp. 1960–1962.
M. van Exter, et al., "Characterization of an Optoelectronic Terahertz Beam System", *IEEE Transactions on Microwave Theory and Techniques*, vol. 38, No. 11, Nov. 1990, pp. 1684–1691.
R. Lipkin, "T Rays for Two—Terahertz waves give rise to a new imaging technique", *Science News*, vol. 148, No. 9, Aug. 26, 1995, pp. 136–137.
R. DeMeis, "Terahertz pulses creat diffraction–limited images", *Laser Focus World*, Jul. 1995, p. 15.
B. B. Hu, et al., "Imaging with terahertz waves", *Optics Letters*, vol. 20, No. 16, Aug. 15, 1995, pp. 1716–1718 (w/Fig. sheet).

P. R. Smith, et al., "Subpicosecond Photoconducting Dipole Antennas", *IEEE J. Quan. Elec.*, vol. 24, No. 2, Feb. 1988, pp. 255–260.

P. Uhd Jepsen, et al., "Radiation patterns from lens–coupled terahertz antennas", *Optics Letters*, vol. 20, No. 8, Apr. 15, 1995, pp. 807–809.

Jenkins & White, *Fundamentals of Optics*, 4th Ed., NY McGraw–Hill, 1976, pp. 167–167.

*Primary Examiner*—Michael J. Tokar
*Assistant Examiner*—Richard Hanig
*Attorney, Agent, or Firm*—Brian K. Dinicola; Gregory C. Ranieri

[57] ABSTRACT

Optical system architectures with improved spatial resolution are provided in which the radiation useful for THz spectroscopy and other investigative procedures can be directionally coupled, in a highly efficient manner, into and out of photoconductive structures such, for example, as dipole antennas. An optical system constructed in accordance with an illustrative embodiment of the present invention comprises a source for emitting radiation in a range of frequencies within from 100 GHz to 20 THz, a coupling lens structure for coupling radiation emitted by said source into free space, at least one collimating optical element for collimating received coupled radiation into a beam having a substantially frequency independent diameter and substantially no wavefront curvature, and a detector for detecting the beam collimated by the at least one collimating optical element. In an optical system constructed in accordance with another embodiment of the present invention, a modified substrate lens structure is used and the collimating optical element is replaced by at least one optical element that focuses received coupled radiation onto a diffraction limited focal spot on or within the medium under investigation.

21 Claims, 5 Drawing Sheets

OPTICAL SYSTEM EMPLOYING TERAHERTZ RADIATION

FIELD OF THE INVENTION

The present invention relates generally to systems and methods of investigating various media or objects using reflected or transmitted radiation in the terahertz or far-infrared region of the spectrum and, more particularly, to arrangements for guiding and focusing the radiation in such systems.

BACKGROUND OF THE INVENTION

The terahertz, or far-infrared region of the electromagnetic spectrum has some unique features. For example, THz waves easily penetrate most nonmetallic objects like paper, cardboard, plastics, and moderate thickness of many dielectrics, yet are absorbed by polar materials and liquids. Carriers in semiconductors show strong dielectric response in this region, while metals are completely opaque to THz radiation. Polar gases such as water vapor, ammonia, HCl etc. have strong and very characteristic absorption lines in this region of the spectrum. Consequently, the THz spectral range is becoming increasingly important for applications such as remote sensing of gases, quality control of plastic and composite materials, package inspection, and moisture analysis. These features can also be used for imaging in the THz frequency range [Nuss, IEEE Circuits and Devices, Mar. 1996]. In addition, the terahertz frequency range has also been of considerable interest in spectroscopy. For example, the electronic properties of semiconductors and metals are greatly influenced by bound states (e.g., excitons and Cooper pairs) whose energies are resonant with THz photons.

The THz regime also coincides with the rates of inelastic processes in solids, such as tunneling and quasiparticle scattering. As yet another example, confinement energies in artificially synthesized nanostructures, like quantum wells, lie in the THz regime.

Despite its potential, the use of THz electromagnetic signals for spectroscopy and imaging has been hindered by a lack of suitable tools. For example, swept-frequency synthesizers for millimeter- and submillimeter-waves are limited to below roughly 100 GHz, with higher frequencies being heretofore available only through the use of discrete frequency sources. Fourier transform infrared spectroscopy (FTIR), on the other hand, remains hampered by the lack of brightness of incoherent sources. Additionally, FTIR methods are not useful if the real and imaginary part of response functions must be measured at each frequency. Finally, real-time imaging using the THz range of the electromagnetic range has not been possible so far due to the poor sensitivity of detectors in this frequency range In U.S. patent application Ser. No. 08/388,933 entitled "Method and Apparatus for Terahertz Imaging" and assigned to the assignee herein, Lucent Technologies, a new spectroscopic imaging technique which overcomes the aforementioned deficiencies was disclosed, which application is expressly incorporated herein by reference in its entirety. This Terahertz ("T-ray") technique is based on electromagnetic transients generated opto-electronically with the help of ultrashort laser pulses (i.e., on the order of several femtoseconds (fs) or shorter). These THz transients are single-cycle bursts of electromagnetic radiation of typically less than 1 picosecond (ps) duration. Their spectral density typically spans the range from below 100 GHz to more than 5 THz. Optically gated detection allows direct measurement of the terahertz electric field with a time resolution of a fraction of a picosecond [Smith et al., IEEE J. Quantum Electr., vol 24, 255–260, 1988]. From this measurement, both the real and imaginary part of the dielectric function of a medium, which medium may be a solid, liquid, or gaseous composition, may be extracted in a rapid, straight-forward manner. Furthermore, the brightness of the THz transients exceeds that of conventional thermal sources, and the gated detection is several orders of magnitude more sensitive than bolometric detection.

Beyond the characterization of new materials and the study of basic physical phenomena, there is a growing appreciation for the many potential commercial applications in which terahertz spectroscopy and imaging might be exploited [Nuss, IEEE Circuits and Devices, Mar. 1996, pp. 25–30]. Promising applications include industrial quality and process control, package inspection, moisture analysis, contamination measurements, chemical analysis, wafer characterization, remote sensing, and environmental sensing. A key ingredient to successful exploitation of any of the aforementioned applications, however, is an optical system which can be efficiently and reliably operated to implement terahertz spectroscopic techniques. In particular, for the above applications, the inventor herein has identified a need for optical arrangements that can first collimate THz signals to a parallel, diffraction-limited beam, and second, focus these terahertz beams to a diffraction limited spot for the best spatial resolution possible. Unlike in optical systems designed for visible light, the wavelength of the THz electromagnetic signals is not negligible compared to the size of the optical elements used, and diffraction effects can dominate ray-propagation, thus complicating the design of optical systems. Furthermore, THz optical beam systems need to perform over the large range of frequencies from below 100 GHz to more than 5 THz covered by the THz signals. This invention overcomes the limitations of the optical systems used in the prior art [Van Exter et al., IEEE Trans. Microw. Theor. Techn., vol. 38, 1684–1691, 1990], such as the inability to generate a parallel, diffraction-limited beam that can be propagated over larger distances with frequency-independent beam diameter, the inability to obtain parallel beams without wavefront curvature [Cheville et al., Appl. Phys. Lett., vol 67, 1960–1962 (1995)], the loss of light due to total internal reflection at the substrate lenses [Jepsen & Keiding, Opt. Lett., vol 20, 807–809, 1995], and the inability to focus broadband THz radiation to a diffraction-limited spot.

SUMMARY OF THE INVENTION

According to the present invention, an optical system with improved throughput, optical beam properties and spatial resolution is provided in which the radiation useful for terahertz spectroscopy, terahertz ("T-ray") imaging, and other investigative procedures can be directionally coupled, in a highly efficient manner, into and out of THz transceivers such, for example, as photoconductive dipole antennas [Smith et al., IEEE J. Quantum Electr., vol 24, 255–260, 1988]. An optical system constructed in accordance with an illustrative embodiment of the present invention comprises a source for emitting radiation in a range of frequencies within from 100 GHz to 20 THz, a coupling lens structure for coupling radiation emitted by said source into free space, the wavelength of the coupled radiation being greater than 1/100th of the beam diameter at an exit pupil of the coupling lens structure, at least one collimating optical element for collimating received coupled radiation into a beam having a substantially frequency independent diameter and substantially no wavefront curvature, and a detector for detecting the beam collimated by the at least one collimating optical element.

An optical system constructed in accordance with another embodiment of the present invention includes a source for emitting radiation in a range of frequencies within from 100 GHz to 20 THz, a first coupling lens structure for coupling radiation emitted by said source into free space, at least one optical element for focusing received coupled radiation onto a diffraction limited focal spot, and a detector for detecting the radiation focused by said at least one optical focusing element.

BRIEF DESCRIPTION OF THE DRAWINGS

The features and benefits of the invention will be better understood from a consideration of the detailed description which follows taken in conjunction with the accompanying drawings, in which.

DETAILED DESCRIPTION OF THE INVENTION

Figure 1:
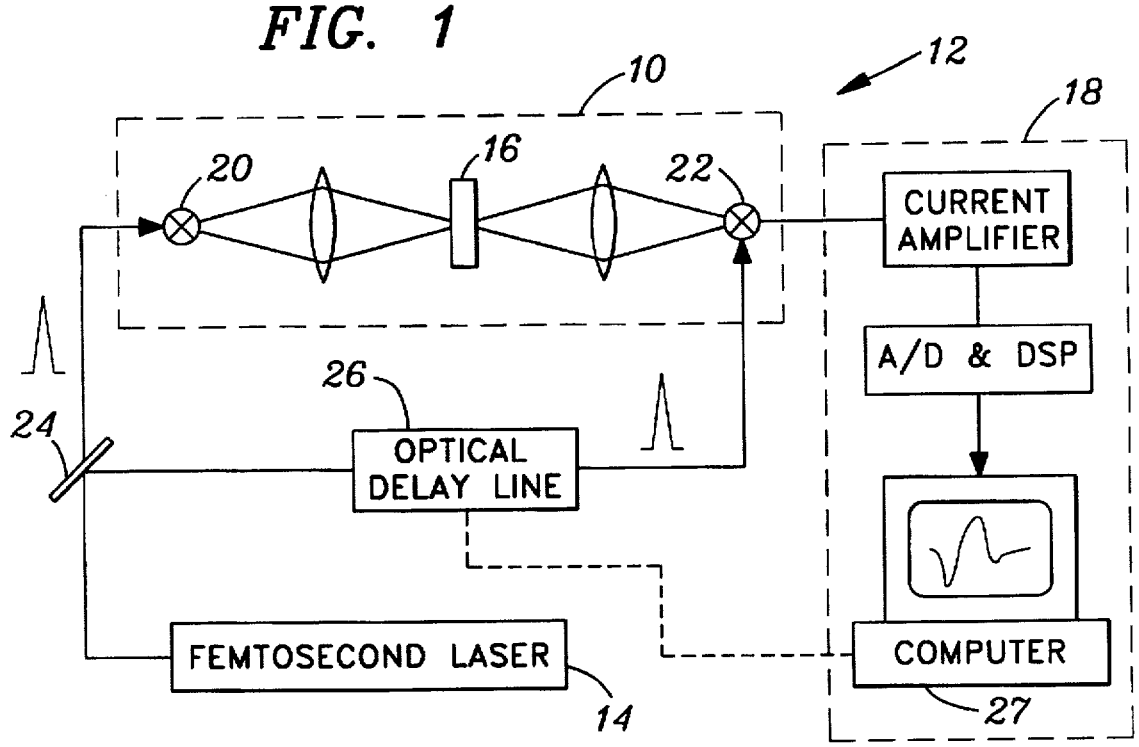
FIG. 1 depicts an arrangement of optical elements, in accordance with an illustrative embodiment of the present invention, as used in an imaging system employing THz radiation focused to a diffraction-limited spot.

An arrangement 10 of optical elements capable of focusing terahertz beams to the diffraction limit in accordance with an illustrative embodiment of the present invention is shown in FIG. 1. For illustrative purposes, the arrangement 10 is shown deployed in an imaging apparatus 12 of the type disclosed in U.S. patent application Ser. No. 08/388,933 entitled "Method and Apparatus for Terahertz Imaging". It will, however, be readily appreciated by those skilled in the art that a lens arrangement constructed in accordance with the present invention has much wider applicability, with exemplary applications including remote sensing, ranging, and composition analysis.

In any event, and with continued reference to FIG. 1, it will be seen that illustrative imaging apparatus 10 includes a source 14 of repetitive optical pulses of femtosecond duration, arrangement 10 by which THz radiation is generated, directed at a medium under investigation such as object 16, and detected upon transmission through or reflection by the medium, and analysis circuitry indicated generally at 18. Source 14 may be configured, for example, as a solid state laser like the Ti:Sapphire laser, which has a wavelength near 800 nm and a typical repetition rate of about 100 MHz. Alternatively, source 14 may be configured as a femtosecond Erbium-Doped Fiber Laser operating at a wavelength near 1.5 µm. In the illustrative embodiment depicted in FIG. 1, arrangement 10 includes an optically gated THz transmitter 20 and an optically gated THz detector 22. A beam splitter 24 divides the output of source 14 into two beams, the pulses of which are used to optically gate transmitter 20 and detector 22. A variable delay line 26, under the control of computer 27, varies the optical delay between the respective gating pulses.

In a preferred embodiment, transmitter 20 and detector 22 are configured as photoconductive switches and consist of a semiconductor bridging the gap in a transmission line structure deposited on the semiconductor substrate surface. The materials used in the fabrication of the photoconductive switches is determined by the operating wavelength of the optical source employed. Materials suitable for photoconductive switches to be used in conjunction with femtosecond lasers operating at wavelengths shorter than about 800 nm include, for example, radiation damaged silicon-on-sapphire (RD-SOS), GaAs, and low temperature grown GaAs (LT-GaAs). By way of additional example, materials suitable for fabricating photoconductive switches to be used with lasers operating at wavelengths around 1.5 µm include low temperature grown InGaAs or InGaAs/InAlAs Quantum Wells [Takahashi et al., Appl. Phy. Lett., Vol. 65 pp. 1790–1792 (1994)].

In the transmitter, a voltage is applied across the photoconductor. The current through the switch rises very rapidly after injection of photocarriers by an optical pulse, and then decays with a time constant given by the carrier lifetime of the semiconductor. The transient photocurrent radiates into free space according to Maxwell's equations. In the detector, a current to voltage amplifier (or ammeter) replaces the voltage bias. The electric field of an incident THz pulse provides the driving field for the photocarriers. Current flows through the switch only when both the THz field and the photocarriers are present. Since electronics are not fast enough to measure the THz transients directly, repetitive photoconductive sampling is used. If the photocarrier lifetime, $\tau$, is much shorter than the THz pulse, the photoconducting switch acts as a sampling gate which samples the THz field within a time τ. Because the laser pulses which trigger the transmitter and gate the detector originate from the same source, the entire THz transient can be mapped by using variable optical delay line 26 to move the photoconductive gate across the THz waveform.

Figure 2:
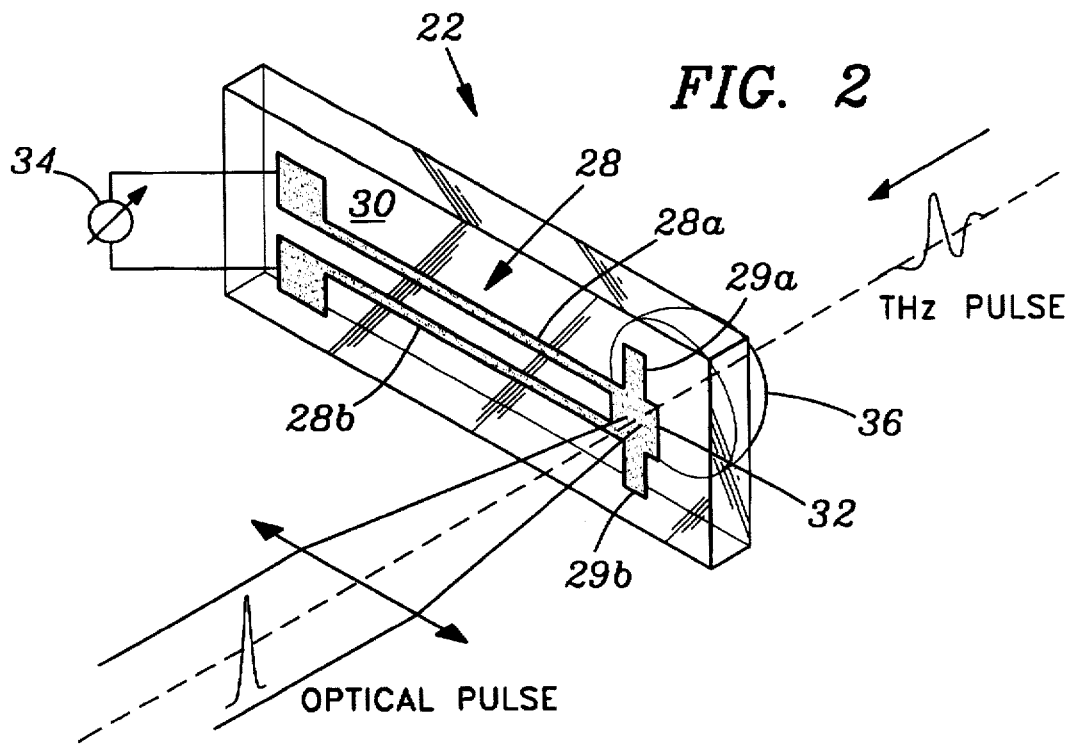
FIG. 2 is a perspective view of a photoconducting dipole antenna detector structure that may be employed in the embodiment of FIG. 1, the antenna structure shown being similar in construction to the transmitter.

In accordance with the embodiment of the present invention depicted in FIG. 1, the THz transmitter 20 and receiver 22 are incorporated into the optical arrangement 10, along with imaging elements that guide the radiation from source to detector and focus the radiation to a diffraction-limited spot on a potentially small sample. In FIG. 2, there is shown a photoconducting dipole antenna structure which is employed in the construction of both the transmitter 20 and the detector 22, with only the detector configuration being specifically shown. Detector 22 comprises a dipole antenna 28 comprising a pair of dipole feed lines 28a and 28b, and optionally, a pair of dipole arms 29a and 29b, fabricated on a substrate 30 of photoconductive materal which, in the illustrative embodiment of FIG. 2, comprises radiation damaged silicon-on-sapphire (RD-SOS). The total dimension of each of the two dipole arms is typically in the range of 10–200 microns with an illustrative gap of about 5 microns extending between them. After formation of the antenna, the silicon layer—which is typically on the order of 0.6 microns thick, is etched away except for a 100×100 square micron area beneath the dipole. This arrangement increases the dark resistance and reduces the dark current of the antenna, which current can be a source of noise for the detector.

In the dark, the photoconductive gap 32 of the dipole antenna is highly resistive (about 20 MΩ). Injection of carriers by the laser pulse causes the resistance to drop below 500 Ω. During the photocarrier lifetime, a current flows which is proportional to the amplitude of the received THz field. As discussed above, the current is converted to a voltage by a current amplifier 34 connected across the feed lines of the antenna. A substrate lens 36 couples the incident THz radiation from free space into the dipole antenna.

Substrate lens 36 is an important element of both transmitter and receiver dipole antennas employed in the optical arrangement 10 of the present invention. Without this lens, the coupling into free space would be limited by the excitation of slab modes between the substrate surfaces. Also, the substrate lens increases the collimation of the emitted electromagnetic radiation. Additionally, the lens serves to magnify the dipole antenna and thus increase its efficiency. Preferably, the dielectric constant of the substrate lens as lens 36 matches that of the underlying substrate 30 in order to minimize reflections at the substrate/lens interface. In the case of GaAs, sapphire, and silicon substrates, high resistivity silicon lenses are especially preferred because of their low THz absorption, frequency independent refractive index, cubic crystal structure, and ease of cutting and polishing.

Figure 3A:
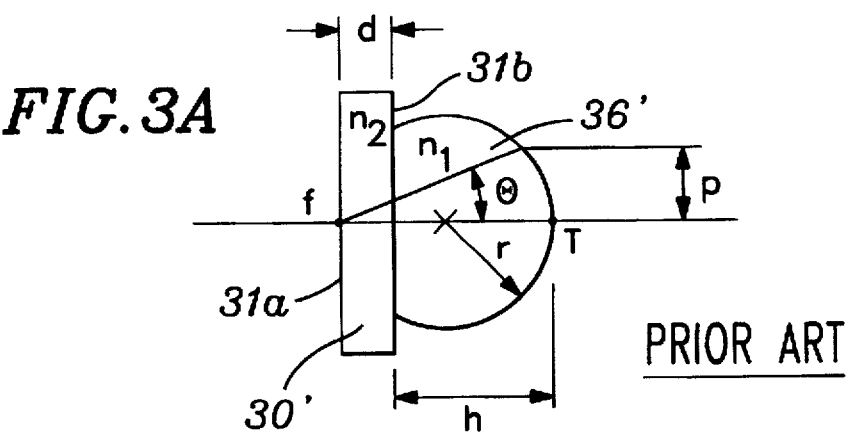
FIG. 3A depicts a conventional substrate lens structure typically employed by the prior art in conjunction with dipole antenna structures such as the one shown in FIG. 2.
Figure 3B:
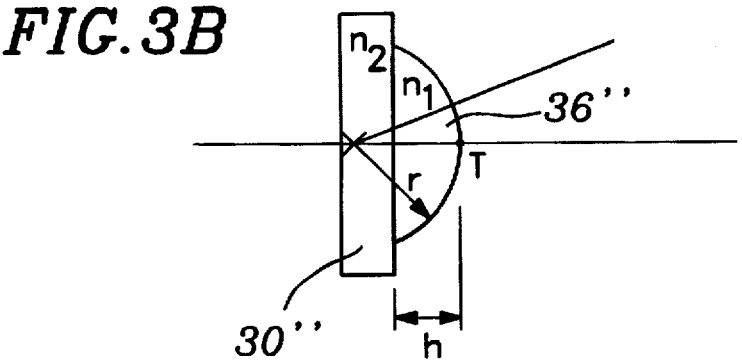
FIG. 3B shows one substrate lens configuration which may be employed in optical arrangements constructed in accordance with the present invention.
Figure 3C:
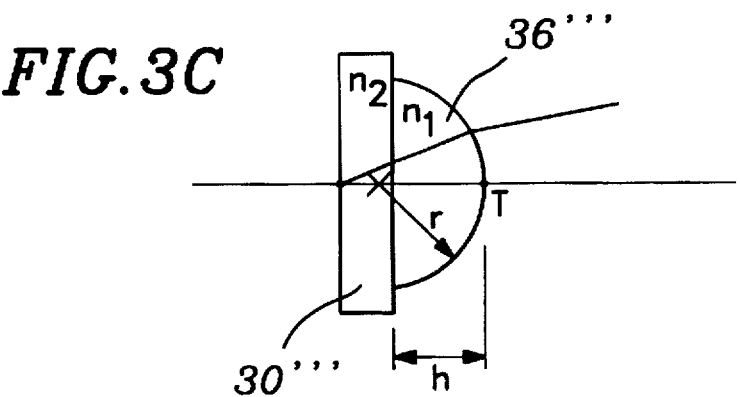
FIG. 3C shows another substrate lens configuration which may be employed in optical arrangements constructed in accordance with the present invention.

Three possible substrate lens configurations are depicted in FIGS. 3A–3C, respectively. The dipole (not shown) is conventionally located on a first surface 31a of the substrate 30', while the substrate lens 36' is attached to the second surface 31b of the substrate. The size of the lenses may be on the order of between 2 and 10 mm in diameter. In the conventional design used in the prior art (FIG. 3A), the dipole source is located at the focal point $f$ of the lens and all rays exit the lens at normal incidence to the substrate. See, for example, van Exter & Grischkowsky. IEEE Microw. Theor. Techn., vol 38, 1684–1691, (1990). In this design, the lens is cut off at a distance h, from the tip T of the lens, given by:

$$h = r\left(\frac{n_1}{n_1-1}\right) - \frac{n_1}{n_2} d$$

where r is the radius of the spherical substrate lens, $n_1$ is the index of the lens, $n_2$ is the index of the substrate, and d is the thickness of the substrate.

Because of the small exit pupil p of the beam at the substrate lens-air interface, diffraction effects destroy collimation of the THz beam, resulting in a beam that cannot be propagated over larger distances without significant spreading and wavefront curvature, and certainly cannot be collimated into a parallel, diffraction limited beam as assumed in the prior art. The inventors herein have recognized, however, that because the source of radiation is a nearly ideal point source, a different substrate configuration can be used to achieve a parallel, diffraction-limited beam with frequency-dependent beam diameter and without wavefront curvature, which can also be focused to a diffraction-limited spot size. In addition, the inventors have realized that in the lens configuration of FIG. 3A, the cone angle over which radiation is emitted is disadvantageously limited to the angle for total internal reflection at the lens to free-space interface. For the lens configuration of FIG. 3A, the maximum cone angle is given by:

$$\sin\theta = \frac{n-1}{n^2-2n}$$

where θ is the half cone angle and n is the refractive index of the substrate lens. Illustratively, for a silicon lens having a refractive index of 3.42, the half cone angle is about 30°. Since the cone angle emitted from a photoconductive dipole is typically larger than the angle derived above (e.g., 45°), a significant fraction of the light emitted from the dipole will be lost due to total internal reflection.

A substrate lens configuration in accordance with the present invention, which may be used to provide substantially parallel beams with substantially frequency-independent diameter and improved spatial resolution in a manner to be described later, is the hemispherical design as shown in FIG. 3B. No refraction occurs at the substrate lens-air interface, so that there is no critical angle for total internal reflection, and consequently, no diffraction effects occur at the exit pupil of the lens. The design specification for the hemispherical lens is such that the center C of the lens 36" is located at the dipole antenna (not shown). To accommodate the thickness of the substrate, the lens is cut off at a distance h from the tip T of the lens given by $$h = r - \frac{n_1}{n_2} d$$

An especially preferred substrate lens configuration in accordance with the present invention has an aplanatic, hyperhemispherical shape and is shown in FIG. 3C. The substrate lens configuration of FIG. 3C may, for example, be employed in combination with an arrangement of lenses and/or mirrors to focus the THz beam down to a diffraction limited spot comparable to the wavelength dimension (e.g., on the order of 300 microns). Like the hemispherical design, it has no spherical aberrations or coma, and when using silicon as a lens material, no chromatic dispersion. The lens is cut off at a distance h from the tip T of the lens given by $$h = r\left(1 + \frac{1}{n_1}\right) - d\left(\frac{n_1 - n_2}{n_2} - 1\right)$$

where r is the radius of the lens, and $n_1$ and $n_2$ are the effective refractive indices of the lens 36''' and substrate 30''', respectively. In contrast to the hemispherical design of FIG. 3B, the aplanatic, hyperhemispherical configuration of FIG. 3C provides slight collimation of the beam, which allows the remaining optical system to be designed with higher f-number optics. In the configuration of FIG. 3C, the critical cone angle for total internal reflection at the lens to free-space interface is large enough to couple substantially all THz radiation emitted by the photoconductive dipole antenna into free space.

Various implementations of the aforementioned hemispherical and hyperhemispherical lens configurations which illustrate their utility will now be described in detail with particular reference to various arrangements of optical elements employed in combination therewith. FIGS. 4A–5B depict various arrangements which may be used in combination with the novel substrate lens configurations of FIGS. 3B and 3C. It should be understood that the various arrangements are by way of illustration only and that either substrate lens configuration may be used in any of the illustrated optical arrangements. In accordance with the present invention, for example, paraboloidal mirrors (or lenses) are used to collimate the transmitted THz radiation to a substantially parallel beam with a beam diameter that does not significantly depend on wavelength or frequency in the range of interest (i.e., 100 GHz to 5 THz). Focusing mirrors or lenses are used to focus the thus collimated parallel beam to a diffraction limited spot in the center of the optical system. A symmetrical arrangement of lenses and mirrors is used to collect the THz radiation efficiently onto the detector.

Figure 4A:
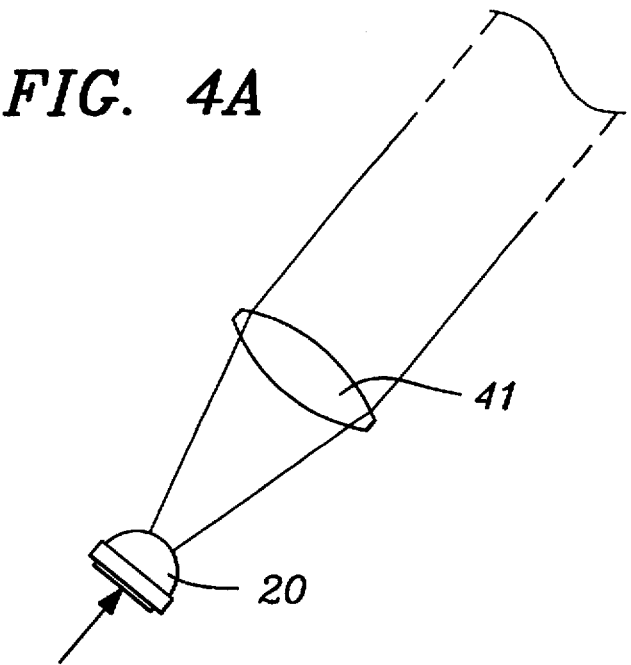
FIG. 4A depicts an illustrative optical arrangement constructed in accordance with the present invention and operable to collimate direct THz radiation, coupled into free space by the substrate lens configuration of 3B or 3C, to a parallel and diffraction-limited beam with substantially frequency independent beam diameter that can be propagated over larger distances with substantially no wavefront curvature.

FIG. 4A depicts an illustrative optical arrangement constructed in accordance with the present invention which utilizes the aplanatic hemispherical substrate lens configuration of FIG. 3B or the aplanatic hyperhemispherical substrate lens configuration of FIG. 3C to generate a collimated beam of THz radiation. According to the invention, the beam B is collimated by at least one optical element—illustratively a single lens 41—to a parallel and diffraction-limited beam having a substantially frequency independent beam diameter that can be propagated over larger distances with substantially no wavefront curvature. In that regard, it should be noted that a collimated beam with no wavefront curvature and a completely frequency dependent beam diameter can only be achieved with the aplanatic hemispherical arrangement of FIG. 3B. With the arrangement of FIG. 3C, on the other hand, a beam that is substantially free of wavefront curvature and that has a substantially frequency independent diameter can only be achieved. Since the numerical aperture of the optical elements required for collimating and/or focusing the THz beams needs to be much larger for the configuration of FIG. 3B it will generally be more practical to employ the aplanatic hyperhemispherical configuration.

Figure 4B:
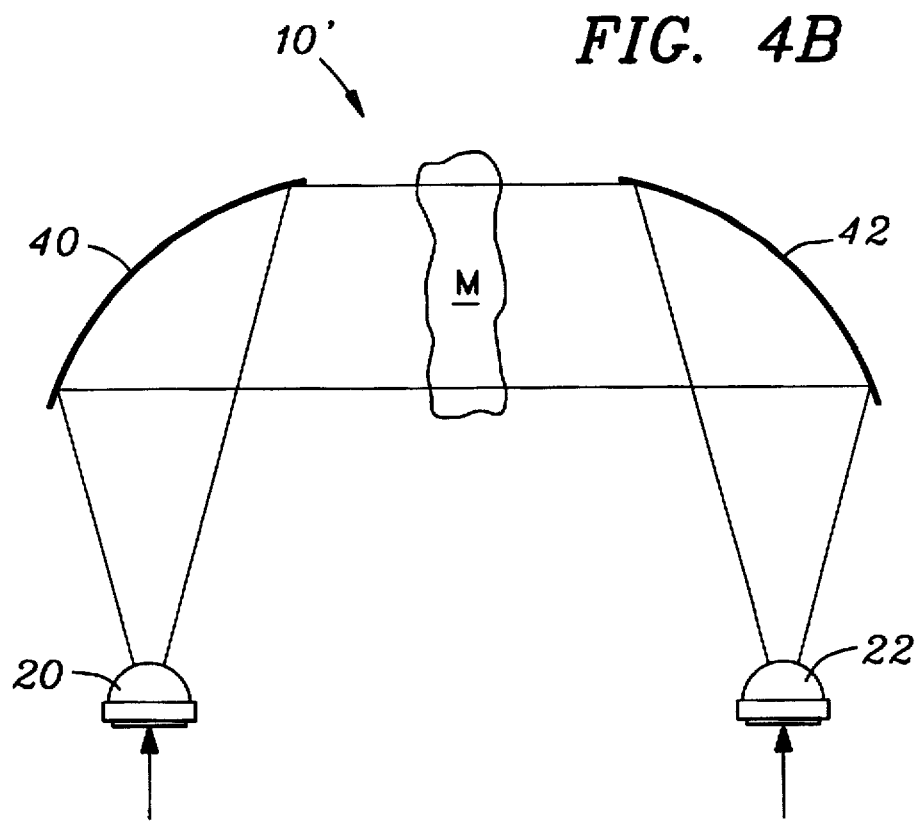
FIG. 4B depicts an illustrative optical arrangement constructed in accordance with the present invention and operable to direct a collimated beam of THz radiation at a medium under investigation for subsequent detection of the portion transmitted therethrough.

In FIG. 4B, there is shown an illustrative embodiment of an optical arrangement 10' constructed in accordance with the present invention which utilizes the aplanatic hemispherical substrate lens configuration of FIG. 3B or the aplanatic hyperhemispherical substrate lens configuration of FIG. 3C to generate a collimated beam of THz radiation and detect that portion of the beam that has been transmitted through a medium under investigation, indicated generally as reference numeral M. In the arrangement depicted in FIG. 4B, off-axis paraboloid mirrors 40, 42 are used to collimate the THz radiation received from transmitter 20 and focus the same on receiver 22.

Illustratively, the full emission or cone angle of the THz radiation emerging from the hyperhemispherical substrate lens is about 30 degrees. Using off-axis paraboloids with a focal length of 6.6 cm, the far-infrared radiation can be collimated to a parallel, diffraction limited beam of roughly 25 mm in diameter. Such a collimated beam, with a substantially frequency independent beam diameter, is especially useful for spectral analysis of objects or media which are inhomogeneous across the diameter of the beam. This configuration also enables the collimated beam to be propagated over large distances (at least several meters) without loss of radiation due to diffraction. In contrast, with prior art configurations using the substrate lens configuration of FIG. 3A, the optimum coupling efficiency is only obtained when the spacing between paraboloids 40 and 42 is twice their focal length. In the above example, the mirror spacing would be 13.2 cm. An additional disadvantage of the prior art configuration is that the THz beam can not be propagated without wavefront curvature. See, for example, Cheville & Grischkowsky, Appl. Physics Lett., vol 67, 1960–1962 (1990). Having beams without wavefront curvature is important for timing analysis of transmitted or reflected THz waves such as, for example, in ranging and time domain reflectometry.

It should be noted that although paraboloid mirrors are somewhat difficult to align, they offer high reflectivity and achromatic operation over the entire THz range. As an alternative, fused quartz lenses may be used at frequencies below 1 THz, and silicon lenses up to 10 THz. It should be further noted, however, that optical alignment of fused quartz lenses using visible laser beams is not practicable since the refractive index is very different at visible and THz frequencies. Another useful lens material is TPX (poly-4-methyl-pentene-1), a polymer which has low absorption and dispersion throughout the THz range but which is somewhat difficult to polish because of its softness.

Figure 4C:
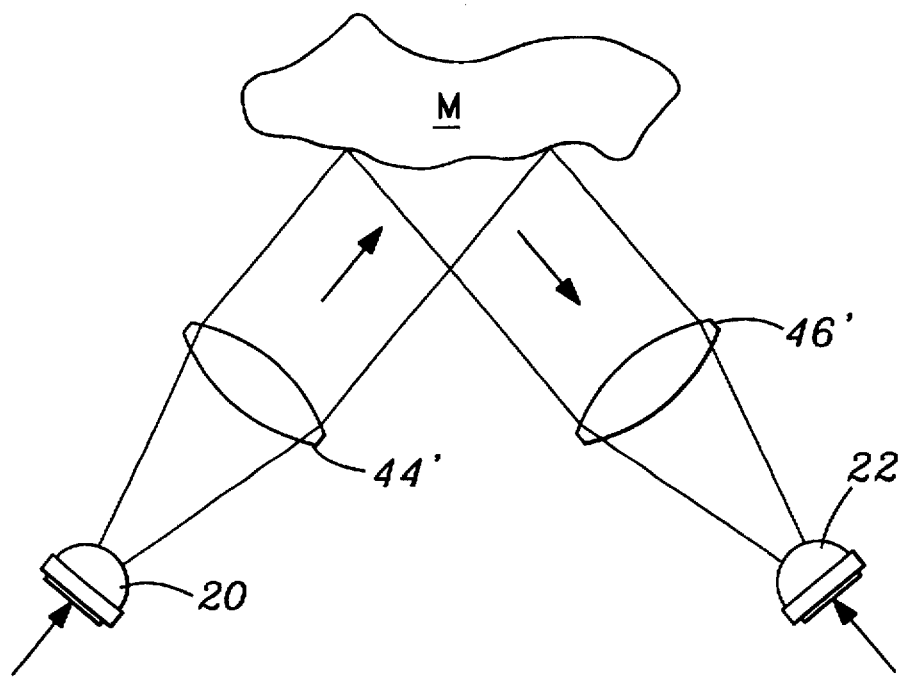
FIG. 4C illustrates another optical arrangement constructed in accordance with the present invention and operable to direct a collimated beam of THz radiation at a medium under investigation for subsequent detection of the portion reflected thereby.

FIG. 4C depicts an arrangement of optical elements in accordance with another illustrative embodiment of the present invention adapted for detection of THz radiation following reflection off the medium M under investigation. In FIG. 4C, focusing lens 44' collimates the beam leaving the transmitter 20 into a beam having substantially no wavefront curvature and a substantially frequency-independent beam diameter in the collimated region. The reflected portion of the beam is coupled into detector 22 by a second focusing lens 46'. Although a reflective arrangement is shown in FIG. 4C, it will be readily appreciated that the configuration depicted can also be configured for transmissive analysis by appropriate arrangement of the respective elements.

Figure 5A:
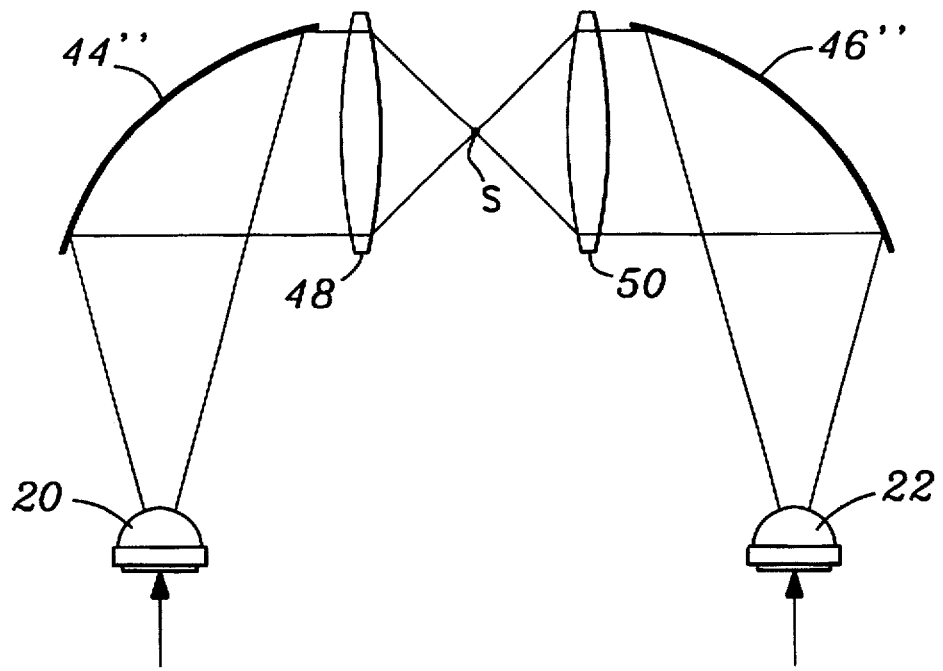
FIG. 5A depicts yet another optical arrangement constructed in accordance with the present invention and operable to focus THz radiation, coupled into free space by the substrate lens configuration of 3B or 3C, to a diffraction-limited spot at a medium under investigation for subsequent detection of the portion transmitted therethrough.

In the arrangement of FIG. 5A, the emitted THz beam emerges from the substrate lens of the transmitter 20 and is collimated by a paraboloid mirror 44'' into a beam having substantially no wavefront curvature and a substantially frequency independent beam diameter. As shown in FIG. 5A, the beam may be further focused down to a diffraction limited spot of less than 1 mm diameter at a peak frequency of 1 THz by inserting a focusing lens 48 or, alternatively, another off-axis paraboloid (not shown). A similar arrangement of optical elements including, for example, a lens 50 and paraboloid mirror 46 is employed to collect the transmitted, focussed radation and focus it onto the receiver 22. This configuration provides a diffraction limited focal spot S at the medium under investigation (not shown), which results in the smallest possible focal point. The ability to focus down to a spot of such small size may be advantageously employed, for example, in high-resolution imaging applications (See Nuss, IEEE Circuits and Devices, Mar. 1996, pp. 25–30) or to investigate articles of small size. In broadband THz imaging, the diffraction limited spot size is inversely proportional to the wavelength of the radiation. Hence, higher spatial resolution may be obtained by selectively processing the high frequency content of the THz pulses.

Figure 5B:
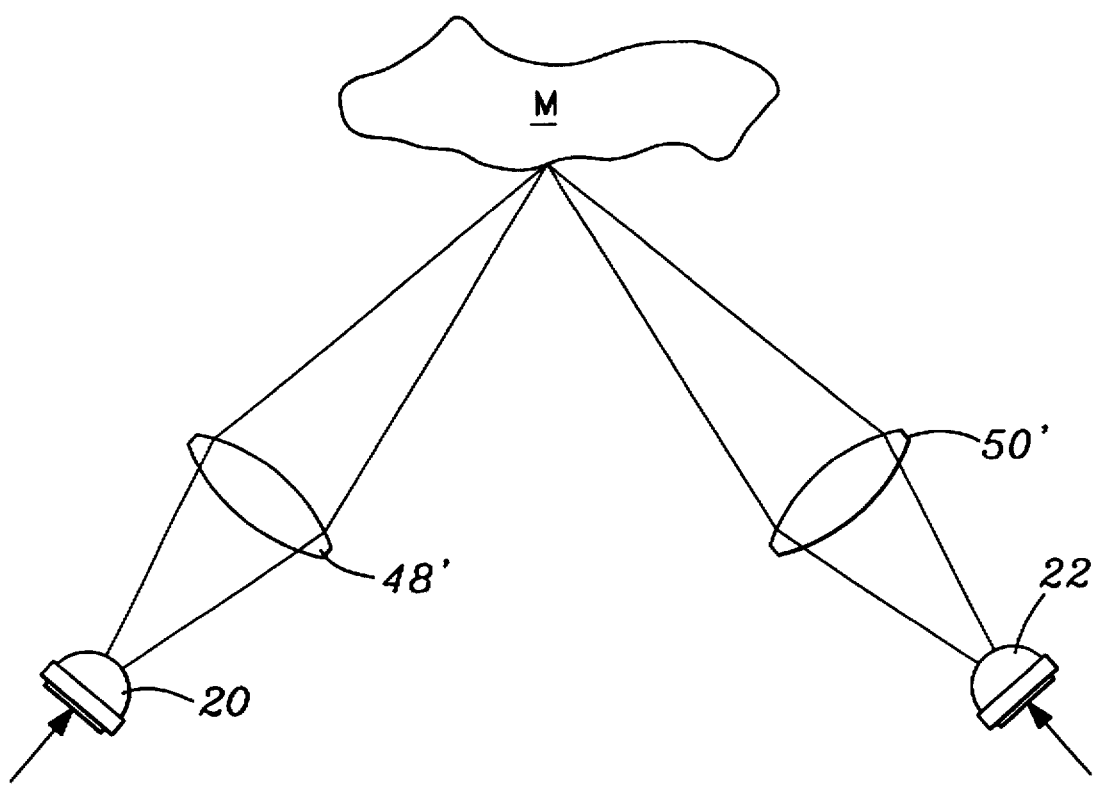
FIG. 5B illustrates a further optical arrangement constructed in accordance with the present invention and operable to focus THz radiation, coupled into free space by the substrate lens configuration of 3B or 3C, to a diffraction-limited spot at a medium under investigation for subsequent detection of the portion reflected thereby.

Turning to FIG. 5B, there is shown yet another arrangement employing an arrangement of optical elements between transmitter 20 and detector 22. The emitted THz beam emerging from the substrate lens of the transmitter 20 is received and focussed to a diffraction limited spot on or within an object or medium M by at least one optical element, such as lens 48'. The radiation reflected from the medium or object is, in turn, collected and focussed on the receiver 22 by a second optical element, such as lens 50'. Again, it should be noted that any number of optical elements may be employed as necessary to collimate and/ focus the THz radiation in a manner suitable for a given application. Moreover, although a symmetrical arrangement is shown throughout the several views, it will be readily ascertained by those skilled in the art that an asymmetrical arrangement of optical elements may also be employed.

The embodiments shown are intended to be merely illustrative of the inventive concepts involved. Various other embodiments and modifications may be made by those skilled in the art without departing from the spirit and scope of the invention.

What is claimed is:

1. An optical system, comprising:
   a source for emitting radiation in a range of frequencies within from 100 GHz to 20 THz,
   a coupling lens structure for coupling radiation emitted by said source into free space, the wavelength of the coupled radiation being greater than 1/100th of the beam diameter at an exit pupil of said coupling lens structure;
   at least one collimating optical element for collimating received coupled radiation into a beam having a substantially frequency independent diameter and substantially no wavefront curvature; and
   a detector for detecting the beam collimated by said at least one collimating optical element.

2. The optical system of claim 1, wherein the source includes a dipole emitter formed on a first surface of a substrate and wherein the coupling lens structure includes a substrate lens formed on a second surface of said substrate, the substrate lens having an optical axis through its center which intersects said dipole emitter.

3. The optical system of claim 2, wherein said substrate lens has a hyperhemispherical shape and wherein the center of said substrate lens and the first surface of said substrate are separated by a distance not greater than the substrate lens radius divided by the refractive index of the lens.

4. The optical system of claim 3, wherein the substrate lens is aplanatic.

5. The optical system of claim 2, wherein the substrate lens is hemispherical.

6. The optical system of claim 2, wherein said substrate lens has a hyperhemispherical shape and wherein the center of said substrate lens and the first surface of said substrate are separated by a distance such that substantially all rays emitted within the dipole radiation cone of the dipole source have an angle of incidence at the lens to free space interface below the critical angle for total internal reflection.

7. The optical system of claim 2, wherein the detector includes a dipole receiver.

8. The optical system of claim 7, wherein the coupling lens is a first coupling lens structure and wherein the detector further includes:
   a second coupling lens structure;
   a concentrating optical element for concentrating collimated radiation onto said second coupling lens structure, said second coupling lens structure being operable to couple the concentrated radiation from free space onto the dipole receiver.

9. The optical system of claim 1, wherein the detector includes an electro-optic receiver.

10. The optical system of claim 1, wherein said at least one collimating element is dimensioned and arranged to direct collimated radiation at a medium under investigation and wherein the detector is arranged relative to said at least one collimating element to receive collimated radiation transmitted through the medium.

11. The optical system of claim 1, wherein said at least one collimating element is dimensioned and arranged to direct collimated radiation at a medium under investigation and wherein the detector is arranged relative to said at least one collimating element to receive collimated radiation reflected by the medium.

12. An optical system, comprising:
   a source for emitting radiation in a range of frequencies within from 100 Ghz to 20 Thz wherein the source includes a dipole emitter formed on a first surface of a substrate;
   a first coupling lens structure for coupling radiation emitted by said source into free space wherein the coupling lens structure includes a substrate lens formed on a second surface of said substrate, the substrate lens having an optical axis through its center which intersects said dipole emitter and wherein the substrate lens is aplanatic and has a hyperhemispherical shape and wherein the center of said substrate lens and the first surface of said substrate are separated by a distance not greater than the substrate lens radius divided by the refractive index of the lens;
   at least one optical element for focusing received coupled radiation onto a diffraction limited focal spot; and
   a detector for detecting the radiation focused by said at least one optical focusing element.

13. A lens arrangement for use in an optical system, comprising:
   a first coupling lens structure for coupling radiation emitted, in a range of frequencies from 100 GHz to 20 THz, by a source into free space; and
   at least one collimating optical element for collimating received coupled radiation into a beam having a substantially frequency independent diameter and substantially no wavefront curvature, the wavelength of the emitted radiation being greater than 1/100th of the beam diameter at an exit pupil of said coupling lens structure.

14. The lens arrangement of claim 13, wherein the coupling lens structure includes a substrate lens formed on a first surface of a substrate.

15. The lens arrangement of claim 14, wherein said substrate lens has a hyperhemispherical shape and wherein the center of said substrate lens and a second surface of said substrate are separated by a distance not greater than the substrate lens radius divided by the refractive index of the lens.

16. The lens arrangement of claim 15, wherein the substrate lens is aplanatic.

17. The lens arrangement of claim 14, wherein the substrate lens is hemispherical.

18. The lens arrangement of claim 13, wherein the coupling lens structure is a first coupling lens structure, further including:

a second coupling lens structure; and a concentrating optical element for concentrating collimated radiation onto said second coupling lens structure, said second coupling lens structure being operatively arranged to couple the concentrated radiation from free space onto a receiver.

19. A lens arrangement for use in an optical system, comprising:

a first coupling lens structure for coupling radiation emitted, in a range of frequencies from 100 Ghz to 20 Thz, by a source into free space wherein the coupling lens structure includes a substrate lens formed on a first surface of a substrate and wherein said substrate lens has a hyperhemispherical shape and wherein the center of said substrate lens and a second surface of said substrate are separated by a distance not greater than the substrate lens radius divided by the refractive index of the lens; and at least one optical element for focusing received coupled radiation onto a diffraction limited focal spot.

20. The lens arrangement of claim 19, wherein the substrate lens is aplanatic.

21. A method of investigating an object with radiation emitted by source over a range of frequencies within from 100 GHz to 20 THz, comprising the steps of:

coupling, with a first coupling lens structure, the radiation emitted by the emission source such that the wavelength of the coupled radiation is greater than 1/100th of the beam diameter at an exit pupil of the coupling lens structure;

collimating received coupled radiation into a beam having a substantially frequency independent diameter and substantially no wavefront curvature;

directing the collimated radiation at a medium under investigation; and detecting one of radiation reflected by and transmitted through the medium during the directing step.

* * * * *